United States Patent [19]

Smith

[11] Patent Number: 4,786,726

[45] Date of Patent: Nov. 22, 1988

[54] FACTOR IX THERAPEUTIC BLOOD PRODUCT, MEANS AND METHODS OF PREPARING SAME

[75] Inventor: Kenneth J. Smith, Albuquerque, N. Mex.

[73] Assignee: Blood Systems, Inc., Scottsdale, Ariz.

[21] Appl. No.: 53,046

[22] Filed: May 22, 1987

Related U.S. Application Data

[63] Continuation of Ser. No. 816,291, Jan. 6, 1986, abandoned.

[51] Int. Cl.$^4$ .................. C07K 3/28; A61K 35/16
[52] U.S. Cl. ..................... 530/381; 530/383; 530/384
[58] Field of Search ............. 530/384, 381, 383; 514/21.8

[56] References Cited

U.S. PATENT DOCUMENTS

| | | | |
|---|---|---|---|
| 3,560,475 | 2/1971 | Fekete et al. | 530/384 |
| 3,717,708 | 2/1973 | Wada et al. | 530/384 |
| 3,893,991 | 7/1975 | Fekete et al. | 530/384 X |
| 4,073,886 | 2/1978 | Kehm | 530/384 X |
| 4,081,432 | 3/1978 | Delente et al. | 530/381 X |
| 4,411,794 | 10/1983 | Schwinn et al. | 530/384 X |
| 4,465,623 | 8/1984 | Chanas et al. | 530/384 |

OTHER PUBLICATIONS

Nature, 315:683–685 (1985), Anson et al.
Nature, 316:268–270 (1985), de la Salle et al.
Nature, 316:271–273 (1985), Busby et al.
Nature, 256:495–497 (1975), Kohler et al.
Methods in Enzymology, 73.3–46 (1981), Galfre et al.
Thrombosis Research, 33, 211–224 (1984), Smith et al.
J. Biol. Chem. 253 (17), (1978), 5946–5951, Osterud et al, Methods in Enzymology, 80 (1981), 221–228, Miletich et al.
Preparative Biochemistry, 11(4), 397–412 (1981), Bajaj et al.
Blood, 59, No. 3 (1982), 664–670, Goodall et al.
Protides of the Biological Fluids, Proceedings of the 13th Colloquium, vol. 30, Feb. 1983, 403–407, Goodall et al.

*Primary Examiner*—Howard E. Schain
*Attorney, Agent, or Firm*—Richard R. Mybeck

[57] ABSTRACT

A method of producing highly purified factor IX from crude factor IX comprising binding an A-7 monoclonal antibody to an Affigel-10 column; partially purifying the crude factor IX to produce a partially purified factor IX; applying that factor IX to the A-7-Affigel-10 column with an application buffer; washing the column with 1-3M NaCl in 0.05M Tris-HCl, 20 mM MgCl$_2$ and 1 mM Benzamidine HCl; eluting purified factor IX from the washed column with 20 mM EDTA; and separating purified factor IX from the EDTA. An improved factor IX product produced thereby.

11 Claims, 2 Drawing Sheets

FACTOR IX THERAPEUTIC BLOOD PRODUCT, MEANS AND METHODS OF PREPARING SAME

INTRODUCTION

This is a continuation of my prior U.S. patent application Ser. No. 816,291, filed Jan. 6, 1986, now abandoned.

The present invention relates generally to blood component therapy and more particularly to unique means and methods of purifying factor IX from prothrombin complex concentrates or other sources of factor IX including culture supernatants containing factor IX from recombinant DNA technology. An improved therapeutic blood product will be prepared using the present invention.

BACKGROUND OF INVENTION

Blood component therapy, made possible by the development of a closed system of multiple plastic collecting bags and high speed refrigerated centrifuges, is one of the most important advances in the history of blood transfusion practices. The rationale for use of specific fractions of blood is that blood contains a number of differently formed elements as well as various plasma proteins and constituents which have many functions. Thus, a single donation of a unit of whole blood can provide red blood cells, platelets, plasma, and cryoprecipitated factor VIII - fibrinogen concentrate. Pheresis procedures are able to supply large quantities of granulocytes, platelets, and plasma from single donors. Plasma can be chemically fractionated to provide albumin or plasma protein fraction, factor VIII concentrate, factor IX complex and immune serum globulin.

The rationale for using blood components is that a patient usually requires replacement of only a specified component (See: Greenwalt et al: *General Principles of Blood Transfusion*, A.M.A. Editorial Board, 1978). Remaining components can be then used to treat patients who require other specific components thereby allowing several patients to benefit from each unit of donated blood thereby maximizing the benefit realizable therefrom.

Factor IX complex is a lyophilized pooled plasma derivative rich in Factors IV, VII, IX and X. It is an alternative to plasma therapy. It supplies vitamin K-dependent clotting factors in a much smaller volume than plasma but with a significantly higher hepatitis risk.

Factor IX containing concentrates are a unique and highly valuable blood product which are life-saving when used to control bleeding in patients suffering with factor IX deficiency (Hemophilia B). These products have also been used to treat those patients inflicted with Hemophilia A having inhibitors although clinical verification of this application is still in progress. Factor IX containing concentrates are also used to arrest serious hemorrhages or to avert operative and post operative bleeding in patients with other congenital clotting factor deficiencies and for multiple factor deficiency induced by an overdose of warfarin-type drugs, i.e., oral anticoagulants.

Commercial concentrates of factor IX have been previously prepared using ion exchange resins to bind vitamin K-dependent clotting factors and separate these proteins from the bulk of other plasma proteins. These clotting factor concentrates are then eluted from the resin and vialed for therapeutic use without further purification. Such concentrates tend to be thrombogenic probably because they contain extraneous vitamin K-dependent clotting factors and/or phospholipid. Further, such concentrates have been a suspected vehicle in the transmission of viral diseases including hepatitis and acquired immune deficiency syndrome ("AIDS"). Further, crude concentrates of factor IX are not stable in vitro and therefore cannot be used for constant infusion therapy which limits its value in chronic replacement therapy.

Recent efforts to create factor IX using a recombinant DNA approach have been frustrated by the difficulty encountered in separating factor IX from culture supernatants with currently accepted techniques. (See: Anson DS, Austen DEG, and Brownlee GG. "Expression of active human clotting factor IX from recombinant DNA clones in mammalian cells." *Nature* 1985;315:683–685; de la Salle H, Altenburger W, Elkaim R, Dott K, et al. "Active γ-carboxylated human factor IX expressed using recombinant DNA techniques." *Nature* 1985;316:268–270; and Busby S, Kumar A, Joseph M, Halfpap L, Insley M, et al. "Expression of active human factor IX in transfected cells." *Nature* 1985;316:271–273).

Thus a very special need exists for the development of means and methods for the manufacture and isolation of highly purified factor IX by affinity chromatography and which can thereafter be formulated into a potent, quick-acting, therapeutic blood product which is stable in vitro and which provides effective relief for patients encountering a critical bleeding incident.

It is to the resolution of that need that the present invention is directed which provides a cell line and method of producing a unique antibody therefrom which antibody is exceptionally suited for purifying factor IX complex and thereby permits the production of a high purity factor IX therapeutic blood product therefrom.

SUMMARY OF THE INVENTION

The present invention relates to the utilization of A-7 monoclonal antibody obtained from mouse ascites or tissue culture supernatants to purify a crude factor IX complex irrespective of which divalent ion is present and to permit the production of an improved purified therapeutic blood product therefrom which product possesses enhanced effectiveness in controlling bleeding incidents arising from a deficiency of clotting factor IX.

The A-7 monoclonal antibody of the present invention is uniquely suited for use in affinity chromotography to purify factor IX complex by separating extraneous protein therefrom and by its unique ability to specifically bind factor IX. More particulary, the present invention is predicated upon my discovery of a novel and unique method of obtaining purified factor IX from crude factor IX complex by coupling a unique A-7 antibody to agarose and like matrices including polyacrylamide, cellulose, and cellulose derived membrane in a column into which a specially buffered factor IX concentrate-benzamidine solution is flowed until the factor IX enzyme is selectively extracted therefrom. The purified factor IX concentrate is then recovered using buffered ethylene diamine tetraacetic acid ("EDTA"), or ethylene glycol-bis(β-amino-ethyl ether)-N,N, N',N'- tetraacetic acid ("EGTA") or sodium citrate and is thereafter concentrated and packaged after its release from the column. The principal advantages of the A-7 Antibody of the present invention are that binding to factor IX is reversible and factor IX can be separated from the matrix without destroying factor IX biologic activity.

Accordingly a prime object of the present invention is to provide improved methodology for producing A-7 monoclonal antibody from mouse ascites and thereafter utilizing that antibody to obtain purified factor IX from crude factor IX complex, or to recover factor IX from tissue culture supernatants where factor IX has been produced by recombinant DNA technology, and to provide an enhanced factor IX therapeutic blood product therefrom.

Another object of the present invention is to provide new and unique methods and reagents for the manufacture of an improved therapeutic blood product having enhanced effectiveness in controlling bleeding incidents of the type associated with clotting factor deficiencies such as Hemophilia B and the like.

A further object of the present invention is to provide an improved therapeutic blood product containing highly purified Factor IX characterized by its quick action, in vitro stability when used to counteract bleeding incidents resulting from clotting factor deficiencies in inadvertent over-dosage with anti-coagulant drugs.

Still another object of the present invention is to provide new and improved reagents for use with affinity chromotography techniques to react with crude factor IX complex and adsorb the factor IX therefrom in a condition for ready elution after all extraneous proteins have been washed therefrom.

These and still further objects as shall hereinafter appear are fulfilled by the present invention in a remarkably unexpected fashion as can be readily discerned from a careful reading of the following detailed description of a preferred embodiment thereof, especially when read in conjunction with the accompanying drawing.

BRIEF DESCRIPTION OF THE DRAWING

The drawing comprises a schematic flow sheet of the preparation of the hybridoma, the use of the hybridoma to produce ascites containing antibody, the selection and purification of A-7 antibody, and the use of A-7 antibody to purify crude Factor IX.

DESCRIPTION OF THE PREFERRED EMBODIMENTS

Figure 1A:
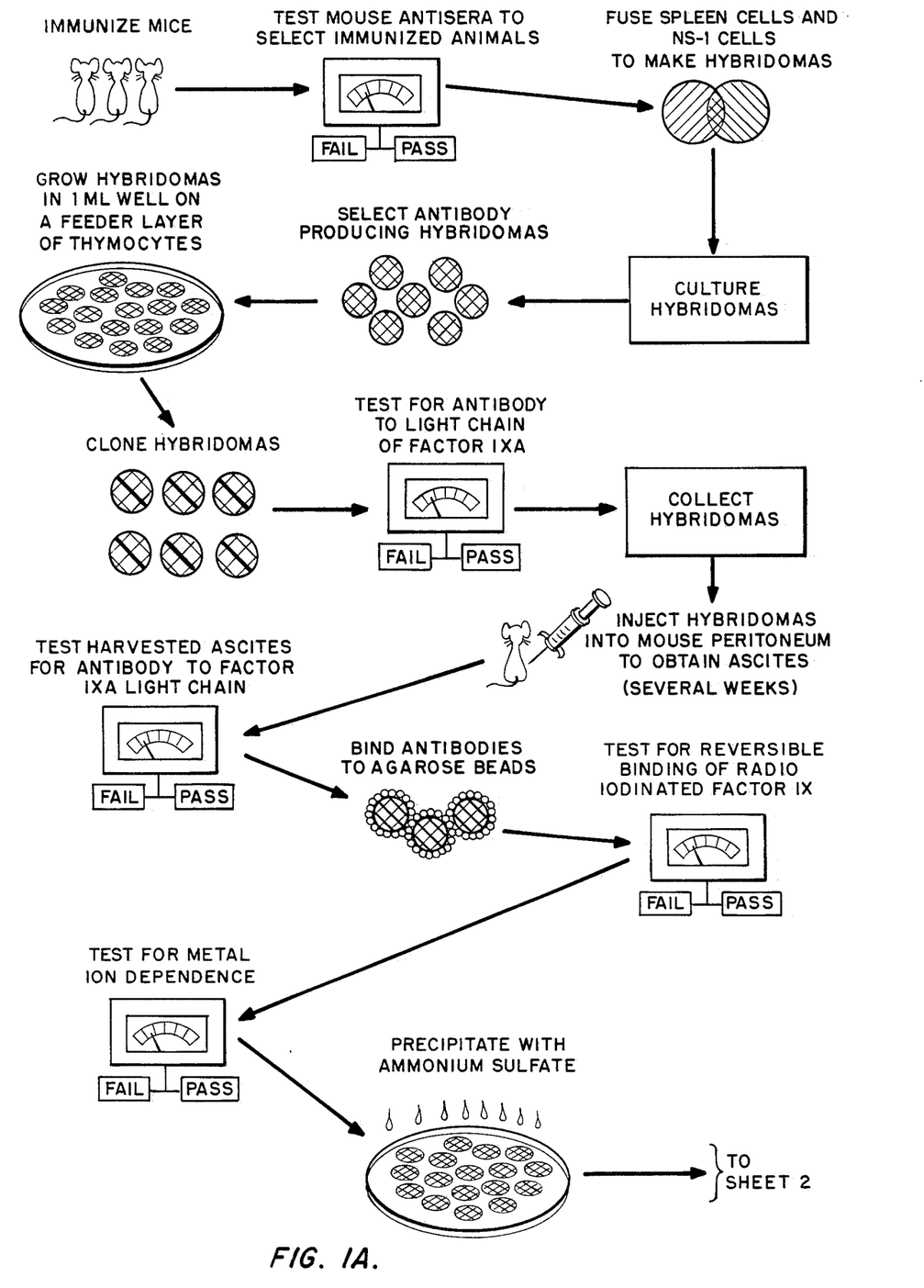
Figure 1B:
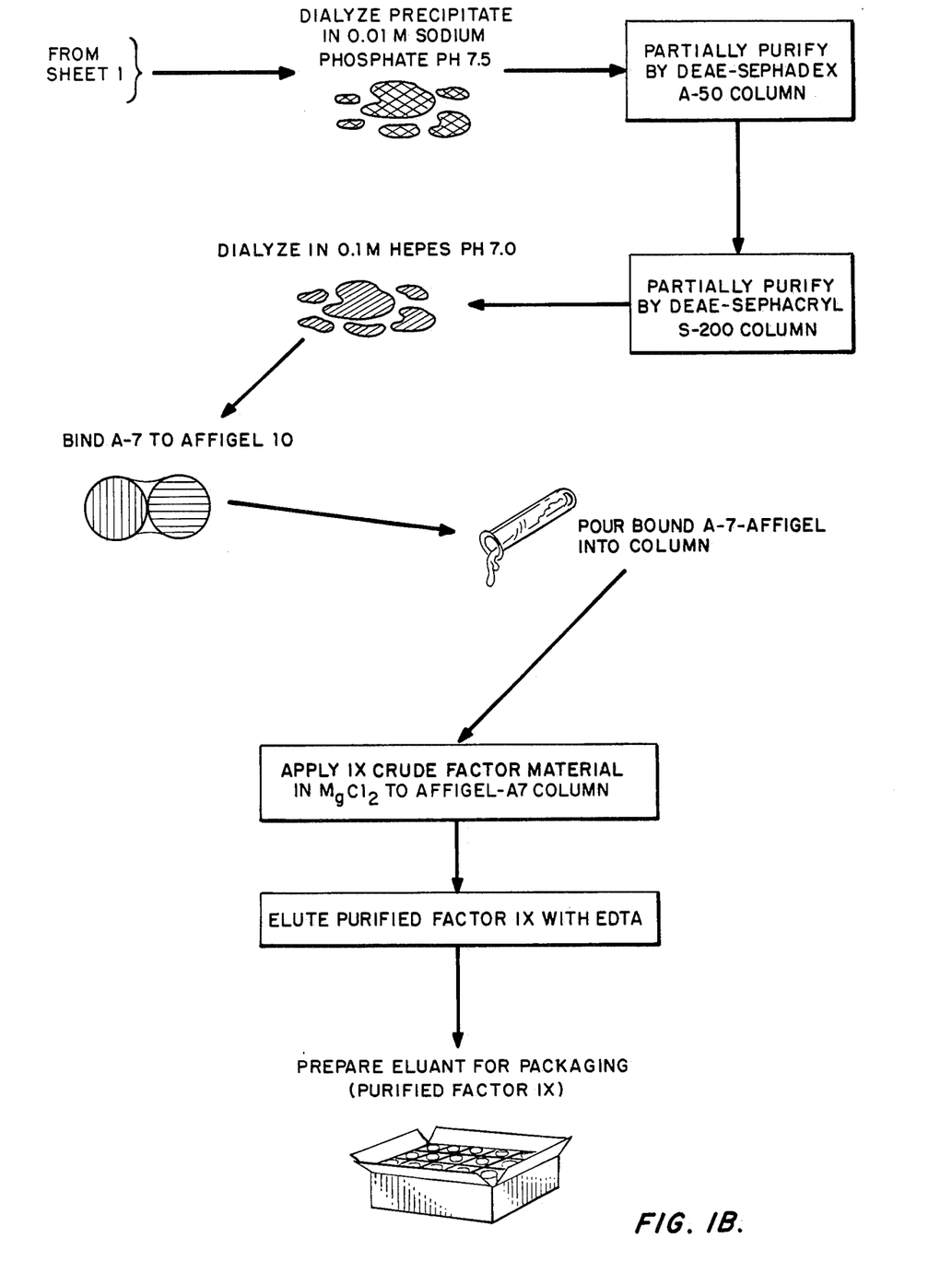

In one practice of the present invention, reference being made to the accompanying drawing a monoclonal antibody used for purifying is obtained from mouse ascites. The A-7 producing hybridoma is injected into the peritoneal cavity of mice given intraperitoneal pristane (0.5 cc) 1-10 weeks previously using the procedure of Galfre and Milstein (Preparation of monoclonal antibodies: Strategies and procedures. *Methods in Enzymology*, Vol 73, Immunochemical Techniques, Part B, New York; Academic Press, 1981: 3-46.) Mice are given cyclophosphamide (20 micrograms per gram body weight) one day prior to intraperitoneal injection of the hybridoma using the technique described by Galfre and Milstein (Op. cit).

HYBRIDOMA PRODUCTION

The hybridoma is prepared as outlined below following the procedures of G. Kohler, C. Milstein, "Continuous Cultures of Fused Cells Secreting Antibody of Predefined Specificity", *Nature,* 1975; 256:495-497.

Immunized mice were selected on day 50-60 of the immunization schedule (see Section C below) for I.V. injection of 10 micrograms of factor IX.

Seventy-two hours after I.V. injection a mouse was sacrificed by ether inhalation and spleens were removed. The mouse spleen was made into a single cell suspension by mincing and forcing it through a 60 mesh screen washed with 7.0 ml of RPMI (GIBCO, Grand Island, N.Y.) containing 10% heat inactivated horse serum (GIBCO), 5% NCTC (Whittaker MA Bioproducts, Walkerville, Md.), 1% pyruvate (GIBCO), and 1% penicillin-streptomycin additives (GIBCO). The suspended cells were layered over 1.5 ml horse serum in a conical centrifuge tube for 10 minutes and supernatant cells were then sedimented at 1000 RPM for 10 minutes in a table-top centrifuge (Damon/IEC Division, Needham Heights, Mass., Model HM-S).

Red cells were lysed in 0.83% $Na_4Cl$ for 10 minutes and sedimented again prior to suspension in 5 ml RPMI without horse serum.

NS-1 cells (N.I.G.M.S. Human Genetic Mutant Cell Depository, Corriell Institute for Medical Research, Copewood St., Camden, N.J. 08103) were sedimented and washed with Roswell Park Memorial Institute Media ("RPMI") and suspended in 5 ml RPMI without horse serum. Spleen and NS-1 cells were counted and checked for viability, $10^8$ spleen cells were added for $10^7$ NS-1 cells and sedimented together and washed with 10 ml RPMI without horse serum.

A 30% solution of polyethylene glycol PEG 1000 (J.T. Baker, Phillipsburg, N.J.) was prepared in RPM without horse serum at 42° C. This mixture was cooled to 37° C. and 0.2 ml added to the cell pellet which was resuspended by tapping. The suspension was sedimented immediately at 1000 revolutions per minute (rpm) for six minutes and after two additional minutes, 5 ml of RPMI without horse serum was added dropwise. After two additional minutes the cells were gently resuspended by a Pasteur pipette. The suspension was centrifuged for five minutes and then resuspended in HT medium (RPMI/20% Horse Serum/1% antibiotics/5% NCTC/ hypoxanthine $1\times10^{-6}M/1.6\times10^{-8}M$ thymidine/1% Pyruvate).

Fifty microliters of the hybridomas in HT medium were then added to each well of a 96-well plate and at 24 hours, 50 microliters of HT medium in $8\times10^{-7}$ M aminopterin was added. HT medium was then added every four days with $4\times10^{-7}$ M aminopterin until NS-1 cells were dead and hybridomas were growing.

Wells with growth were fed with HT medium and then RPMI. Hybridoma supernatants were tested for antibody by ELISA as described below (see Section C) for testing of mouse antisera.

Hybridomas producing antibody were stabilized by growing them in 1.0 ml wells prior to mass culture and freezing.

In order to transfer the hybridomas to 1.0 ml wells, a feeder layer of mouse thymocytes was made. Thymus cells from one-month-old mice were made into a single cell suspension as detailed for spleen cells with the exception that RPMI contained 10% horse serum/5% NCTC/1% antibiotic mixture/1% pyruvate. This suspension was made to $5\times10^6$ cells/ml and 1 ml was added to a 24-well microliter plate prior to addition of the hybridoma from the microliter wells.

Cloning was done by limiting dilution technique after cells were growing in 1 ml wells. Hybridoma cells, at dilutions of 20 cells and 6 cells/ml, were added in fifty microliter aliquots to microliter wells containing 50 microliters of thymocyte feeder layer at $2\times10^7$ cells/ml.

Hybridomas were retested by ELISA and then either grown up for injection into mice as detailed below or frozen in 10% dimethylsulfoxide (DMSO) (Sigma, St. Louis, Mo.) in RPMI at $10^7$ cells/ml in the vapor phase of liquid nitrogen.

TEST FOR ANTIBODY SPECIFICITY

As discussed (K. Smith, K. Ono, "Monoclonal Antibodies to Factor IX", *Thrombosis Research*, 1984; 33:211-224), the A-7 antibody was selected for its ability to bind to the light chain of factor IXa (amino acids 1-145) on immunoblotting. It was believed that this region would contain the metal ion dependent antigens useful for the immunoaffinity purification of factor IX (herein denominated "antibody A-7").

Factor IX was cleaved by factor XIa for immunoblotting. Factor IX was incubated with factor XIa in a 1:20 ratio of enzyme to substrate in 0.1M NaCl 0.05M Tris (pH 8.0) with 10 mM $CaCl_2$ at 37° C. for one hour. Greater than 90% dodecyl activation was demonstrated on sodium dodecylsulfate polyacrylamide gel electrophoresis (SDS-PAGE). After activation, factor IXa was mixed with an equal volume of sample solution for SDS-PAGE to stop the reaction. Protein preparations were analyzed using the protocols of Weber and Osborn (Weber, K. and Osborn, M., "The reliability of molecular weight determinations by dodecyl sulfate-polyacrylamide gel electrophoresis." *J. Biol. Chem.* 244, 4406-4412, 1969.) or La emmli (La emmli, U.K., "Cleavage of structural proteins during the assembly of the head of bateriophage T4." *Nature*, 227, 680-685, 1970.), using 10% polyacrylamide slab gels. For Weber and Osborn gels, samples were mixed with an equal volume of sample solution containing 20 mM Tris-HCl (pH 8), 2 mM EDTA, 4M urea, 65 mM dithiothreitol (or 5% 2-mercaptoethanol), and 0.005% Bromophenol Blue and heated for one minute in a boiling water bath. Samples containing equal amounts of factor IX and factor IXa were then applied to slab gels at a density of 2 micrograms of protein per cm of gel application point and electrophoresed at 50 mA/gel for six hours.

After electrophoresis, mixtures of factor IX and factor IXa and other vitamin K dependent proteins were transferred to nitrocellulose sheets (Millipore Corp., Bedford, Mass.), using a Trans-Blot cell from Bio-Rad Laboratories, Richmond, Calif.. The transfer buffer was 0.192M glycine 25 mM Tris-HCl (pH 8.3) with 20% methanol. Transfer at 30 volts and 0.5 amps took six hours at room temperature. Nitrocellulose sheets were then cut into $5\times150$ mm strips and incubated overnight with 3% purified Bovine Serum Albumin (BSA) in phosphate buffered saline (0.15M NaCl/.01M $NaPO_4$, pH 7.2) (PBS) at room temperature. Purified monoclonal antibody at 100 μg/ml in 0.15M NaCl/0.02M Tris-HCl (TBS) with 5 mM $CaCl_2$ and 1 mM $MgCl_2$ or undiluted hybridoma supernatants were then incubated with the nitrocellulose strips for six hours and washed in three changes of PBS with 0.05% Tween 20 or 0.15M NaCl 0.02M Tris-HCl (pH 7.2) with metal ions. Strips were incubated with rabbit anti-mouse kappa light chain (Miles, Elkhart, Ind.) diluted 1:100 in PBS containing 3% BSA for two hours or TBS containing 3% BSA with metal ions. $^{125}$I-labeled staphylococcal protein A ($2\times10^6$ cpm/ml) in 3% PBS-BSA or TBS with metal ions was incubated with the strips for two hours since this radioactive ligand binds to rabbit IgG. After three changes of wash solution, strips were dried and analyzed by autoradiography. Nitrocellulose strips were placed in an x-ray cassette with Kodak XRP-1 film and an intensifying screen at −70° C. Films were developed in a clinical x-ray processor after 1-12 exposure.

Hybridoma supernatants or purified antibodies reacting with the light chain of factor IXa were further characterized.

The hybridoma producing the A-7 antibody (FIG. 1B in K. Smith, K. Ono, "Monoclonal Antibodies to Factor IX", *Thrombosis Research*, 1984; 33:211-224), was tested for metal ion dependence after larger amounts of antibody were produced in mouse ascites (as detailed below). Antibody was purified and coupled to agarose as hereinafter detailed.

TESTS FOR REVERSIBLE FACTOR IX BINDING AND METAL-ION DEPENDENCE

Twenty-five microliters of a 50% suspension monoclonal A-7 coupled to agarose beads at a concentration of 3 mg antibody per ml of wet gel were added to test tubes containing 1.0 ml 0.15M NaCl/0.02M Tris-HCl (pH 7.2) with 1 mg/ml BSA. Replicates of this mixture were then made to 5 mM $CaCl_2$ or 1 mM EDTA for comparison of effects of no added metal ions, calcium, and EDTA on antibody binding. See the drawing.

Factor IX was iodinated with $^{125}$I by the chloramine T technique (A. R. Thompson, "Factor IX Antigen by Radioimmunoassay", *J. Clin. Invest.*, 1977; 59:900-910) at a specific activity of 1.6 μCi/μg protein. One hundred microliters of a 300 nM solution of radiolabelled factor IX was added to the mixtures of A-7 beads and various ions. The amount of factor IX bound was determined by counting supernatant solution after 4-hour room temperature incubation and centrifugation to remove antibody coated beads. The A-7 antibody showed no factor IX binding in the presence of EDTA and abundant binding with calcium present.

In addition, the A-7 antibody did not bind to solid phase factor IX in the ELISA assay described below (see Section C) when EDTA was present at 1 mM concentration.

PURIFICATION OF LARGE AMOUNTS OF A-7 ANTIBODY

For purification of large amounts of A-7 antibody produced by the hydridoma, ascites fluid is removed by needle and stored frozen at −20° C. until purification. The ascites fluid is treated with 0.1 mM PMSF (phenyl methyl sulfonyl-fluoride, Sigma Chemical Company, St. Louis, Mo.) for 20 minutes at room temperature and all debris removed by centrifugation. Antibody is precipitated by addition of solid ammonium sulfate to 50 percent saturation at 4° C. for 15 minutes. The antibody containing precipitate is obtained after centrifugation (10,000 g for 20 minutes) and washed with 50% saturated ammonium sulfate in 0.15M NaCl/0.05M Tris-HCl (pH 7.5). This and all further steps are performed at 4° C.

The final concentrate obtained after recentrifugation is dissolved in 0.01M sodium phosphate pH 7.5 and dialyzed overnight against three changes of 100 volumes of buffer. The antibody concentrate is applied to a DEAE Sephadex A50 column (Pharmacia Fine Chemicals, Piscataway, N.J.) of the appropriate size determined by the capacity of the gel following the manufacturer's instructions. The column is washed with 0.01M sodium phosphate until the absorbance at 280 nm reached a level of 0.1 or less in a 1 cm light path and then the protein is eluted using a linear gradient of 0.3M NaCl in 0.01M sodium phosphate and an equal volume of 0.01M sodium phosphate. The total elution volume is six times the column volume.

Antibody containing fractions are detected by an ELISA system using factor IX immobilized on microtiter plates using the technique reported in "Monoclonal antibodies to factor IX: Characterization and use in immunoassays for factor IX." *Thrombosis Research*, 1984; 33:211–224 (See Section C below).

The antibody containing fractions are pooled and concentrated using pressure filtration and a YM-30 membrane and filtration cell (Amicon Corporation, Danvers, Mass.).

The preparation is further purified by Sepacryl S-200 gel filtration in 0.2M NaCl/.01M Tris-HCl pH 7.5 and antibody containing fractions are identified, pooled, and concentrated as discussed above.

An alternative to the ion exchange chromatography described above is to dialyze the ammonium sulfate precipitated antibody in 0.02M Tris-HCl pH 7.2 prior to application to a blue dye and diethylaminoethyl derivatized cross-linked agarose gel bed support ("DEAE-Affigel-Blue" column, BioRad Laboratories, Richmond, Calif.). The protein is eluted using a linear gradient made up with equal volumes of 0.02M Tris-HCl and 0.02M Tris-HCl with 0.15M NaCl. Antibody containing fractions are identified and concentrated as previously described. A further alternative is to apply the antibody to a column of Staphlococcal Protein A linked to Sepharose 4B (Pharmacia, Piscataway, N.J.). Antibody is eluted with 0.1M Glycine-HCl (pH 2.6), dialyzed and concentrated as previously described.

The final concentrate after Sephacryl S-200 gel filtration is then dialyzed against 0.1M HEPES (N-2-hydroxyethyl piperazine-N'-2-ethanesulfonic acid) pH 7.0 for coupling to Affigel 10 (BioRad Laboratories, Richmond, Calif.). In this procedure the gel from the manufacturer is washed in ice-cold deionized water and then mixed with antibody containing solution (10 mg antibody/ml of gel) in volume ratios of 4 to 1 antibody solution to gel.

Alternative procedures for binding to matrices include cyanogen bromide (CNBr) activation of Sepharose 4B (Pharmacia Fine Chemicals, Piscataway, N.J.) as described by Fujikawa. (See: Fujikawa K, Thompson AR, Legaz ME, Meyer RG, and Davie EW. "Isolation and characterization of bovine factor IX (Christmas Factor)". *Biochemistry* 1973; 12:4938–4944.) For an alternative procedure, the carbohydrate of the heavy chain of immunoglobulin can be coupled to matrices as described by Junowicz et al (See: The derivatization of oxidized polysaccharides for protein immobilization and affinity chromatography, *Biochimica et Biophysica Acta* 1976; 428:157–165).

After unbound antibody has been washed from the gel and unreacted sites masked by incubation with 1.0M glycine ethyl ester (pH 8.0) for 1 hour, the gel is equilibrated in 0.05M NaCl-0.05M Tris-HCl pH 7.5 (TBS) with 20 mM magnesium chloride. Factor IX containing commercial concentrates or tissue culture supernatants containing factor IX are treated with magnesium added at a final concentration of 20 mM, and benzamidine HCl 10 mM prior to application to the A-7 matrix. The column used contains a 20-fold excess of antibody to factor IX to be bound by weight.

Commercial concentrate of factor IX (4800U) or factor IX from other sources is dissolved in water according to the manufacturer's directions (Cutter Laboratories, Berkeley, Calif.; Hyland Laboratories, Costa Mesa, Calif.; Alpha Therapeutics, Los Angeles, Calif.). Benzamidine (Aldrich Chemical Co., Milwaukee, Wis.) is added to a final concentration of 10 mM and the concentrate is then mixed with an equal volume of 0.1 M Tris-HCl/0.1M NaCl pH 7.5 with 20 to 40 mM magnesium chloride.

The concentrate thus produced is applied to a 20 ml column of agarose coupled to 200 mg of monoclonal antibody A-7, produced as described above, for 2–6 hours. The column is then washed with two column volumes of 0.05M Tris-HCl/0.05M NaCl pH 7.5 and 6 to 10 column volumes of 1M-3M NaCl in 0.05M Tris-HCl pH 7.5. Washing is continued until there is only minimal protein (less than 20 micrograms per ml) in column effluent as determined by absorbance at 280 nm assuming an extinction coefficient of 10 for a 1% protein solution. The Factor IX is then eluted with 20 mM EDTA in 0.10M NaCl/0.05 Tris-HCl, pH 7.5. Fractions containing protein are then concentrated using a pressure filtration cell and a YM-30 membrane (Amicon Corporation).

Solvent exchange can be accomplished using the pressure filtration cell prior to lyophilization or preparation for infusion.

The highly purified factor IX produced hereby can then be lyophilized for patient delivery using conventional technology when combined with physiologically acceptable excepients such as glucose, maltose, citrate buffered saline, HEPES and the like, including mixtures thereof.

The metal ion-dependent purification process can be implemented with calcium chloride and EGTA or EDTA and other divalent cations, such as manganese followed by EDTA.

This process is particularly suited for purifying factor IX from tissue culture supernatants containing fetal calf serum since the A-7 antibody binds to recombinant factor IX but not to bovine factor IX.

In another practice of the current invention, a monoclonal antibody is purified from tissue culture supernatants. All purification steps are at 4 degrees centigrade. The A-7 antibody is purified from tissue culture supernatant by precipitation after adding ammonium sulfate to a final saturation of 50% at 4 degrees centigrade. The pellet obtained from this material is resuspended in 0.02M Tris-HCl (pH 7.2) and dialyzed prior to chromatography on DEAE-Affigel Blue (Bio-Rad Laboratories, Richmond, Calif.) or DEAE-Sephadex A-50 (Pharmacia Inc., Piscataway, N.J.). The A-7 antibody is separated from contaminating proteins by a salt gradient from 0 to 0.4M NaCl.

Antibody containing fractions are dialyzed in 0.1M HEPES buffer pH 7.0 and concentrated using a YM-30 membrane and a pressure filtration cell (Amicon Corporation, Danvers, Mass.). The antibody is coupled to Affigel 10 (Bio-Rad Laboratories) at a protein content of 10 mg of antibody per one ml of gel by mixing antibody and gel on a rotator overnight. CNBr activated Sepharose 4B (Pharmacia Inc.) or activated Bio-Gel A5M (Bio-Rad Laboratories) can also be used to prepare the matrix for coupling. CNBr-activated Sepharose 4B and CNBr activated Bio-gel A5M must be at pH 9 in 0.1M sodium carbonate buffer.

After washing the matrix and blocking residual sites for coupling with 1M glycine ethyl ester pH 8 (Sigma Chemical Co, Saint Louis, Mo.), the gel is ready for affinity purification procedures.

Other procedures of relevance to the present invention will now be described.

A. Factor IX Purification.

This procedure has been described by Thompson AR, "Factor IX antigen by Radioimmunoassay." *J. Clin. Inves.*, 1977; 59:900–910. All buffers contained 1 mM Benzamidine. Two liters of plasma from normal blood bank donors was treated with 17.58 g $BaCl_2 \cdot 2H_2O$ per liter and the precipitate was recovered by centrifugation. The barium citrate precipitate containing adsorbed vitamin K dependent coagulation factors was washed twice with 0.15M barium chloride, then water. Vitamin K dependent coagulation factors were eluted with 0.15M sodium citrate (pH 7.5). The eluate was diluted with two volumes of water and applied to DEAE-Sephadex A-50 in 0.05M sodium citrate pH 7.5. Factor IX was eluted with an exponential gradient from 0.05M sodium citrate to 0.5M sodium citrate. Fractions containing factor IX were identified by single-stage coagulation factor assay using factor IX deficient plasma. These fractions were pooled and dialyzed in 0.05M NaCl/0.05M Tris-HCl (pH 7.5) prior to application to heparin-Sepharose 4B prepared as reported by Fujikawa K, Thompson AR, Legaz ME, Meyer RG, and Davie EW, "Isolation and Characterization of Bovine Factor IX (Christmas Factor)", *Biochemistry*, 1973; 12:4938–4943. Factor IX was eluted from heparin-Sepharose 4B with a linear salt gradient from 0.05 to 1.0M sodium chloride in 0.05M Tris-HCl with 1 mM $CaCl_2$ (pH 7.5). Factor IX containing fractions were pooled for injection after concentration by precipitation with 65% saturated ammonium sulfate. Precipitated factor IX was resuspended in 0.05M NaCl/0.05M Tris-HCl (pH 7.5) and dialyzed in the same buffer. After dialysis protein content was determined by absorbance at 280 nm using an extinction coefficient of 13.3 for a 1% solution.

B. Immunization.

This is detailed in the article by K. Smith, K. Ono, "Monoclonal Antibodies to Factor IX", *Thrombosis Research*, 1984; 33:211-224 on pages 213-214. Balb/c mice were immunized with 200 µg of factor IX in complete Freund's adjuvant (Difco, Detroit, Mich.), divided into I.P. and S.C. routes. Repeat immunization at days 24 and 41 with 60 µg factor IX in incomplete Freund's adjuvant were also divided for I.P. and S.C. injection. Sera from immunized mice were tested by ELISA, as described below.

C. TESTING IMMUNIZED MICE.

Microtiter plates were coated with factor IX at a concentration of 20 µg/ml in 0.15M NaCl/0.01M $NaHPO_4$ (pH 7.2)(PBS). After overnight incubation at 4° C., plates were washed in PBS and non-specific binding to plates was blocked by adding 200 µl 3% bovine serum albumin in PBS at room temperature for 2 hours.

Plates were then washed with PBS with 1.5 mM $MgCl_2$, 2 mM mercapto ethanol and 0.05% Tween-20 (Sigma, St. Louis, Mo.). Mouse antisera were diluted in the same buffer prior to addition to the plates for 1 hour at 37° C. and 30 minutes at 4° C. Plates were then washed six times with the same buffer to remove unbound antibody prior to addition of β-galactosidase conjugated F(ab')$_2$ fragments of sheep anti-mouse IgG (Bethesda Research Laboratories, Gaithersberg, Md.) diluted 1:200 in the above buffer. Plates were then washed 6 times after a 2-hour room temperature incubation and then 50 microliters of substrate from BRL (1 mg/ml p-nitrophenyl-β-D-galactopyranoside) were added for 15 minutes. Reactions were stopped with an equal volume of 0.5M $Na_2CO_3$. Absorbance was read in an automated microplate reader at 405 nM (Dynatech Laboratories, Alexandria, Va. Model MR-560). Sera from well immunized mice had detectable absorbance at dilutions of greater than $10^6$.

To further aid in the understanding of the present invention, and not by way of limitation, the following examples are presented.

EXAMPLE I

A-7 monoclonal antibody was prepared by purifying ascites obtained from Balb/c mice injected with a hybridoma in the peritoneal cavity into which 0.5 cc pristane had been injected from 1 to 10 weeks previously and cyclophosphamide (20 micrograms per gram body weight) injected 24 hours earlier.

The ascites fluid was removed by needle and stored at −20° C. until purification. For purification, the ascites fluid was treated with 0.1 mM pheny methyl sulfonylfluoride (PMSF) for 20 minutes at room temperature and all debris was then removed therefrom by centrifugation. The antibody was then precipitated by the addition of solid ammonium sulfate to a 50 percent saturation at 4° C. for 15 minutes. The antibody containing precipitate was obtained after centrifugation at 10,000 g for 20 minutes and thereafter washed with 50 percent saturated ammonium sulfate in 0.15M NaCl, 0.05M Tris, pH 7.5 at 4° C.

The final concentrate obtained after recentrifugation was dissolved in 0.01M sodium phosphate (pH 7.5) and dialyzed overnight against three changes of 100 volumes of buffer. This antibody concentrate was then applied to a DEAE Sephadex A50 column and washed with 0.1 sodium phosphate until the absorbance at 280 nm reached a level of 0.1 or less in a 1 cm light path. The protein was then eluted at 4° C. using a linear gradient of 0.3M NaCl in 0.01M sodium phosphate and an equal volume of 0.01M sodium phosphate. The total elution volume was six times the column volume. The antibody containing fractions were detected by the ELISA system and thereafter pooled and concentrated using pressure filtration and a YM-30 membrane and filtration cell (Amicon). The pool was stored at 4° C. for future use.

EXAMPLE II

A sample of factor IX was isolated from plasma obtained from patients undergoing therapeutic plasmapheresis. All purification steps were performed at four degrees centigrade. 294 grams of trisodium citrate dihydrate were added to 100 liters of plasma and the mixture was stirred until the sodium citrate had dissolved. Four liters of 1M $BaCl_2$ were then added and the preparation was stirred for 15 minutes prior to centrifugation at 4000 g for 10 minutes. The supernatant plasma was discarded. The barium citrate precipitate obtained was then twice suspended in 0.15M NaCl with 10 mM $BaCl_2$ and 1 mM Benzamidine and separated from the washing solution by centrifugation at 4000 g for 10 minutes. The barium citrate precipitate was then suspended on 1M Na$_2$SO$_4$ with 5 mM Benzamidine and after stirring for 15 minutes, the sodium sulfate precipitate obtained was then separated from supernatant plasma by centrifugation at 4000 g for 15 minutes. The supernatant was then dialyzed against 0.025 sodium citrate pH 6.0 with 1 mM Benzamidine overnight and then applied to 1000 ml column of DEAE-Sepharose (Pharmacia Fine Chemicals, Piscataway, N.J.). All buffers in the purification procedure contained 1 mM Benzamidine. The factor IX containing fractions were obtained by a linear salt gradient where starting and finishing buffers were 3 liters of 0.025M sodium citrate pH 6.0 and 3 liters of 0.025M sodium citrate pH 6.0 with 0.7M NaCl. The factor IX containing fractions were precipitated by adding solid ammonium sulfate to 65% saturation and then dialyzed overnight in 0.025M sodium citrate pH 7.4 and applied to a 1000 ml column of Dextran-Sulfate agarose prepared by coupling Dextran-Sulfate (Pharmacia Fine Chemicals, Piscataway, N.J.) to cyanogen bromide activated agarose (200 mg Dextran Sulfate per ml of gel). Factor IX containing fractions were obtained by a linear salt gradient with 3 liters of 0.025M sodium citrate (pH 6.5) and 3 liters of 0.025M sodium citrate with 1.0M NaCl (pH 6.5). This partially purified preparation of factor IX was then dialyzed in TBS (0.1M NaCl and 0.05M Tris-HCl pH 7.5 with 1 mM Benzamidine) in preparation for passage over the A-7 antibody column. The washed partially purified factor IX was then applied to a 14 ml column of Affigel-10 having 75 mg of the A-7 antibody (prepared according to EXAMPLE 1) bound thereto which was first extensively washed with TBS (0.1M NaCl, 0.05 Tris HCl, pH 7.5). The application buffer was TBS with 0.1% Tween-20 (Sigma Chemical Co., St. Louis, Mo.), 5 mM MgCl$_2$ and 1 mM Benzamidine-HCl. The column was washed with 3M NaCl in 0.05M Tris-HCl pH 7.5 with 5 mM MgCl$_2$ and 1 mM Benzamidine HCl and factor IX (7.7 mg) was eluted with 20 mM EDTA. Protein purity of factor IX was verified by immunologic testing using goat antisera to factor IX and immunoassays for factor IX using monoclonal antibodies. Clotting activity was verified by the ability of this protein to correct the clotting time of plasma from a patient known to be deficient in factor IX. The eluted protein appeared to be over 95% factor IX as determined by sodium dodecyl sulfate polyacrylamide gel electrophoresis. Clotting activity in units/per milligram was 160, 187 and 313 on three different specimens.

EXAMPLE III

A variation of the method of Example II was conducted using the same A-7 antibody Affigel 10 column, but the source of factor IX was an eluate from barium citrate. In this example, three liters of plasma were obtained from a single individual undergoing therapeutic plasmapheresis. Benzamidine was added to plasma at a final concentration of 1 mM. A barium citrate precipitate was obtained by adding 17.58 grams of BaCl$_2$•2H$_2$O per liter and stirring for 1 hour at 4 degrees centigrade. The precipitate was recovered by cetrifugation at 4000 g for 15 minutes and supernatant plasma was discarded. The precipitate was resuspended in 0.15M BaCl$_2$ with 1 mM Benzamidine and separated from the wash solution by centrifugation at 4000 g for 15 minutes. Protein was eluted from the washed barium citrate precipitate by resuspending twice in 500 ml 0.15M sodium citrate pH 7.5 with 1 mM Benzamidine. The supernatant solution obtained by centrifugation at 4000 g for 15 minutes was then dialyzed in TBS with 1 mM Benzamidine. The eluate was dialyzed in TBS with 1 mM Benzamidine. An aliquot of this preparation was then clarified by precipitating lipoproteins in 8% polyethylene glycol (MW=4000). The factor IX containing material with residual polyethylene glycol was applied to the column and 2.94 mg of factor IX was recovered as previously described.

EXAMPLE IV

A third source of factor IX was tested using the same A-7 Affigel 10 column over a period of 30 days, a total of 25.1 mg of factor IX was purified using Konyne (Cutter Laboratories, Berkeley, Calif.) Lot NC9127 as the starting material. Prior to application to the column, the commercial concentrate of factor IX was made to 10 mM MgCl$_2$ and 10 mM Benzamidine. Specific activity of the purified factor IX was 313 and 386 units per mg.

EXAMPLE V

A larger column of the A-7 antibody was made by coupling 194 mg of antibody A-7 to 55 ml of Affigel 10 and 41.3 mg of factor IX was purified using the same lot of Cutter concentrate as in Example IV. The application buffer (TBS) used consisted of 10 mM MgCl$_2$ and 10 mM Benzamidine. For this larger columns, Factor IX, partially purified as described in Example II, was passed over the column and produced 20.2 mg of purified factor IX.

EXAMPLE VI

A DEAE-Sepharose extract of plasma was used as the source of factor IX. The plasma was obtained from individuals (3 to 12 liters) and treated with 10 mM Benzamidine prior to addition of 80 ml/liter of DEAE-Sepharose which had been equilibrated in 0.025M sodium citrate pH 6.5. After stirring for one hour at room temperature, the Sepharose was collected by filtration and washed with 6 volumes of 0.025M sodium citrate pH 6.5. The factor IX containing fractions were then eluted by a linear gradient of 0.025M sodium citrate (pH 6.5) to 0.5M NaCl in 0.025M sodium citrate (pH 6.5) both with 1 mM Benzamidine. The volume of each buffer was three times the column volume. Protein fractions were then pooled and dialyzed in TBS with 1 mM Benzamidine prior to application to the A-7 antibody column. Magnesium concentration was 20 mM in this case. 32 mg of factor IX were prepared.

EXAMPLE VII

Tests specific to determining the metal ion requirements were conducted which revealed that zinc chloride, copper II acetate, manganese chloride and calcium chloride all allowed factor IX to bind to A-7. Weaker binding was obtained with cadmium chloride, strontium chloride and barium chloride. Mixtures of 1 mM magnesium chloride and 1 mM calcium chloride were nearly as effective as 20-40 mM MgCl$_2$. The A-7 antibody prepared pursuant hereto does not bind bovine factor IX, but does bind to factor IX produced with recombinant DNA technology.

From the foregoing it is apparent that methods and compositions have been herein described and illustrated which fulfill the aforestated objectives in a remarkably unexpected fashion. It is of course understood that such modifications, alterations, and applications as may readily occur to the artisan confronted with this disclosure are intended within the spirit of this invention which is limited only by the scope of the claims appended hereto.

Accordingly, what is claimed is:

1. The method of producing highly purified factor IX from crude factor IX comprising the steps of:
   (a) binding an A-7 monoclonal antibody to an Affigel-10 column;
   (b) partially purifying said crude factor IX to produce a partially purified factor IX;
   (c) applying said partially purified factor IX to said Affigel-10 column having said A-7 antibody bound thereto with an application buffer;
   (d) washing said column with 1M-3M NaCl in 0.05M Tris-HCl, 20 mM $MgCl_2$ and 1 mM Benzamidine HCl;
   (e) eluting purified factor IX from said washed column with 20 mM EDTA; and
   (f) separating said purified factor IX from said EDTA.

2. The method according to claim 1 in which said A-7 antibody is purified before coupling to said Affigel column by adding ammonium sulfate to a 50% saturation at 4° C. to produce an A-7 antibody containing pellet, resuspending the pellet obtained thereby in 0.02 M Tris-HCl at a pH of 7.2, dialyzing said suspension in 0.1 M HEPES buffer at a pH of 7.0; and concentrating said antibody in a pressure filtration cell.

3. The method according to claim 2 in which said A-7 antibody is produced from mouse ascites obtained from preconditioned mice injected with hybridoma.

4. The method according to claim 2 in which said A-7 antibody is obtained from tissue culture supernatants.

5. The method according to claim 1 in which said crude factor IX is in plasma and is partially purified by adsorbing the vitamin K-dependent clotting factors therefrom to a barium citrate precipitate obtained by adding $BaCl_2$ $2H_2O$ to said plasma.

6. The method according to claim 1 in which said application buffer consists of TBS containing 20 mM magnesium chloride and 1 mM benzamidine hydrochloride.

7. The method according to claim 5 in which said application buffer consists of TBS containing 20 mM magnesium chloride and 1 mM benzamidine hydrochloride.

8. The method according to claim 6 in which said A-7 antibody is purified before coupling to said Affigel column by adding ammonium sulfate to a 50% saturation at 4° C. to produce an A-7 antibody containing pellet, resuspending the pellet obtained thereby in 0.02M Tris-HCl at a pH of 7.2, dialyzing said suspension in 0.1M HEPES buffer at a pH of 7.0; and concentrating said antibody in a pressure filtration cell.

9. The method according to claim 8 in which said A-7 antibody is produced from mouse ascites obtained from preconditioned mice injected with hybridoma.

10. The method according to claim 8 in which said A-7 antibody is obtained from tissue culture supernatants.

11. The method according to claim 1 in which crude factor IX is partially purified by adsorption to an ion exchange resin selected from the group consisting of DEAE-Sepharose, QAE (quarternary amino ethyl-)Sephadex DEAE-Sephadex and DEAE-cellulose.

* * * * *

UNITED STATES PATENT AND TRADEMARK OFFICE
CERTIFICATE OF CORRECTION

PATENT NO. : 4,786,726
DATED : November 22, 1988
INVENTOR(S) : Kenneth J. Smith

It is certified that error appears in the above-identified patent and that said Letters Patent is hereby corrected as shown below:

Col. 1, line 45, "IV" should read ---II---;
       line 54, "inflicted" should read ---afflicted---;
Col. 2, line 9, "its" should read ---their---;
Col. 3, line 24, after "action," insert ---and---;
Col. 4, line 4, "a mouse was" should read ---the mice were---;
       line 18, "$Na_4Cl$" should read ---$NH_4Cl$---;
       line 31, "RPM" should read ---RPMI---;
       line 64, "a 24-well microliter" should read ---each well in a 24-well microtiter---;
       line 65, "microliter" should read ---microtiter---;
Col. 5, line 18, delete "(herein denominated "antibody A7")".
       line 23, delete "dodecyl"
       line 32, "La emmli (La emmli" should read ---Laemmli---;
       line 58, after "Tris-HCl" insert ---, pH 7.2---;
Col. 6, line 6, "1-12 exposure" should read ---1-12 hour exposure---;
       line 21, " suspension" should read ---suspension of---;
Col. 7, line 16, "membrane and filtration" should read ---membrane filtration---;
       line 61, "1.0 M" should read ---0.1 M---;
Col. 8, line 17, "pH 7.5" should read ---pH 7.5 with 20 mM

UNITED STATES PATENT AND TRADEMARK OFFICE
CERTIFICATE OF CORRECTION

PATENT NO. : 4,786,726

DATED : November 22, 1988

INVENTOR(S) : Kenneth J. Smith

It is certified that error appears in the above-identified patent and that said Letters Patent is hereby corrected as shown below:

$MgCl_2$---;

line 19, "pH 7.5" should read ---pH 7.5 with 20 mM $MgCl_2$---;

Col. 9, line 4, "1M" should read ---0.1 M---;

line 15, "donors was" should read ---donors were---;

Col. 11, line 40, "EDTA" should read ---EDTA in 0.1 M NaCl/ 0.05 M Tris-HCl, pH 7.5---; and Col. 12, line 28, "consisted of" should read ---contained---.

Signed and Sealed this

Nineteenth Day of September, 1989

*Attest:*

DONALD J. QUIGG

*Attesting Officer*      *Commissioner of Patents and Trademarks*